US009198794B2

(12) United States Patent
Juniman

(10) Patent No.: US 9,198,794 B2
(45) Date of Patent: Dec. 1, 2015

(54) SYSTEM AND METHOD FOR SUPPORTING A DROOPING HEAD AND REHABILITATING THE MUSCLE GROUPS AT CAUSE

(76) Inventor: Marlena L. Juniman, Upper Holland, PA (US)

(*) Notice: Subject to any disclaimer, the term of this patent is extended or adjusted under 35 U.S.C. 154(b) by 612 days.

(21) Appl. No.: 13/447,198

(22) Filed: Apr. 14, 2012

(65) Prior Publication Data

US 2012/0260925 A1 Oct. 18, 2012

Related U.S. Application Data

(63) Continuation of application No. 61/475,568, filed on Apr. 14, 2011.

(51) Int. Cl.
*A61F 5/37* (2006.01)
*A47C 7/38* (2006.01)

(52) U.S. Cl.
CPC .............. *A61F 5/3707* (2013.01); *A47C 7/38* (2013.01)

(58) Field of Classification Search
CPC ........ A61F 5/3707; A47C 7/38; A47C 7/383; A63B 23/025; A63B 21/0552; A63B 21/0555; A63B 21/1407; A63B 21/1415; A63B 21/1449
USPC ................ 128/869, 870, 876, 845–846, 848; 602/17, 18, 36; 297/393, 391; 482/124, 482/10, 121, 131, 907; 5/622, 628, 636, 5/637; 2/175, 171, 310–312, 317, 318
See application file for complete search history.

(56) References Cited

U.S. PATENT DOCUMENTS

| 4,560,201 | A | * | 12/1985 | Scott | 297/393 |
|---|---|---|---|---|---|
| 5,258,017 | A | * | 11/1993 | Myers et al. | 606/241 |
| 5,336,139 | A | * | 8/1994 | Miller | 482/10 |
| 5,372,565 | A | * | 12/1994 | Burdenko | 482/124 |
| 5,830,165 | A | * | 11/1998 | Rowe et al. | 602/4 |
| 5,893,365 | A | * | 4/1999 | Anderson | 128/848 |
| 7,004,545 | B2 | * | 2/2006 | Miller | 297/393 |
| 7,637,261 | B2 | * | 12/2009 | Sharp | 128/848 |
| 7,832,802 | B2 | * | 11/2010 | Ehlers et al. | 297/393 |
| 8,062,241 | B2 | * | 11/2011 | Bonutti | 602/4 |
| 8,613,690 | B1 | * | 12/2013 | Thompson | 482/10 |
| 2008/0139984 | A1 | * | 6/2008 | Tranfic | 602/18 |
| 2011/0054372 | A1 | * | 3/2011 | Murnaghan | 602/18 |
| 2015/0042143 | A1 | * | 2/2015 | Maginness | A47C 7/383 297/393 |

FOREIGN PATENT DOCUMENTS

| GB | 2389509 A | 12/2003 | |
| GB | 2492588 A | * 1/2013 | ............ A61F 5/3707 |

*Primary Examiner* — Victoria J Hicks
*Assistant Examiner* — Kari Petrik
(74) *Attorney, Agent, or Firm* — Ryder, Lu, Mazzeo & Konieczny LLC

(57) ABSTRACT

A system and method for supporting a user's head in an upright position. A strap is provided that has a first end, a second end, a first attachment section proximate the first end, a second attachment section proximate the second end, and a center section. The center section of the strap is anchored to the head of the user. Tension is applied to the strap in order to lift the user's head and hold the user's head in an upright orientation. The tension in the strap is maintained by anchoring the strap to the user's torso. The strap can have elastic characteristics that enable the strap to stretch. As such, the strap can provide resistance to neck movements without preventing those neck movements. This enables muscle groups in the neck to be exercised and provide the possibility of rehabilitation.

13 Claims, 4 Drawing Sheets

SYSTEM AND METHOD FOR SUPPORTING A DROOPING HEAD AND REHABILITATING THE MUSCLE GROUPS AT CAUSE

RELATED APPLICATIONS

This application claims the benefit of U.S. Provisional Patent Application No. 61/475,568, filed Apr. 14, 2011 and entitled Head Support Device, the full disclosure of which is incorporated into this specification by reference.

BACKGROUND OF THE INVENTION

1. Field of the Invention

In general, the present invention relates to devices and methods that are used to support the human head in an upright position. More particularly, the present invention relates to head support systems that use support straps that engage and support the head.

2. Prior Art Description

Dropped Head Syndrome is characterized by severe weakness of certain muscle groups, such as the trapezius, splenius capilis and semispinalis cervicus, that extend up the back of the neck. Weakness in and around these muscle groups cause the head to lean forward. This causes the chin to rest on the chest while a person is standing or sitting. Floppy Head Syndrome and Head Ptosis are other names used to describe this same syndrome. Most of the time, Dropped Head Syndrome is caused by a specific generalized neuromuscular diagnosis. These include amyotrophic lateral sclerosis (ALS) also known as Lou Gehrig's disease, Parkinson's disease, myasthenia gravis, polymyositis, and genetic myopathies. Other specific causes can include motor neuron disease, hypothyroidism, disorders of the spine, and cancer. When the base cause of Dropped Head Syndrome is not known, it is called isolated neck extensor myopathy (INEM). The INEM form of Dropped Head Syndrome usually happens in older persons. The weakness of the muscles in the back of the neck usually occurs gradually over time.

As Dropped Head Syndrome develops, tire head begins to tilt downward. Because of the weakness of the muscle groups in the neck, the chin sinks until it contacts the chest. Lifting or raising the head while sitting or standing soon becomes impossible. When the chin of a person sinks to the chest, the gaze of that person is directed down at the floor, instead of forward. The face has a downward orientation. The neck appears elongated, and the curve at the base of the neck is accentuated. This can cause over stretching or pinching of the spinal cord. When this happens, there may be weakness and numbness of the arms or entire body. Furthermore, the unnatural curvature of the neck can cause difficulties in swallowing, speaking, and/or breathing.

Isolated neck extensor myopathy (INEM) is considered benign because it does not spread or get worse. Symptoms can improve in some cases. Accordingly, it is most often treated conservatively by physicians. Prior art treatments of Dropped Head Syndrome are mainly supportive in nature. The most common prescribed treatment is the use of a neck collar. The wearing of a neck collar can temporarily correct the chin-on-chest deformity. This improves the forward gaze and activities of daily living. It also can help prevent contractures of the neck in a fixed flexed posture. However, the use of a neck collar can be uncomfortable and can cause contact sores under the chin. Furthermore, the use of a neck collar causes the weakened muscle groups in the neck to further atrophy from lack of use. As a result, the Dropped Head Syndrome may become worse when the net collar is removed.

In the prior art, attempts have been made to avoid the use of a neck collar by attaching a restraint to the head and pulling the restraint in tension down the center of the back. The tension in the restraint holds the user's head upright. Such prior art systems are exemplified by U.S. Patent Application Publication No. 2011/0054372 to Murnaghan, entitled, Cervical Spine And Neck Support Device, and United Kingdom Patent Application GB 2,389,509A to Ratchford entitled, A Head Restraint.

A problem associated with such prior art systems is that any restraint that extends down a user's back needs to be anchored to something in order to support the weight of the user's head. The restraint cannot be anchored to a user's clothes or else the clothes simply ride up on the user's body when worn and would become uncomfortable as the user's head drops. As such, prior art systems, such as the cited Murnaghan system, anchor the restraint through the user's groin area. The cited Ratchford system anchors the restraint to an underlying chair in which a user must sit. Such systems are therefore very difficult for a person to wear and are impractical to use in many situations.

Another problem associated with such prior art head support systems is that they simply hold the head upright. No movement of the head against the restraint is permitted. As a result, the weakened muscle groups in the neck are not exercised and still may be subject to atrophy. The consequence is that the Dropped Head Syndrome may become worse.

A need therefore exists for a system and method of supporting a user's head in an upright position, without using a neck collar and without requiring an impractical anchor for a head restraint. A need also exists for a system and method of supporting a user's head in an upright position that exercises the muscle groups of the neck, therein providing rehabilitation and strengthening to those muscle groups.

These needs are met by the present invention as described and claimed below.

SUMMARY OF THE INVENTION

The present invention is a system and method for supporting a user's head in an upright position. A strap is provided that has a first end, a second end, a first attachment section proximate the first end, a second attachment section proximate the second end, and a center section. The center section of the strap is anchored to the head of the user, by either passing the strap over the user's forehead or attaching the strap to a hat worn by the user.

Tension is applied to the strap in order to lift the user's head and hold the user's head in an upright orientation. The tension in the strap is maintained by anchoring the strap to the torso of the user. The strap is anchored to the torso of the user by passing the ends of the strap under the user's arms and joining the sections of the strap across the front of the user's torso.

The strap can have elastic characteristics that enable the strap to stretch. As such, the strap can provide resistance to neck movements without prevents those neck movements. This enables muscle groups in the neck to be exercised and provide the possibility of rehabilitation.

BRIEF DESCRIPTION OF THE DRAWINGS

For a better understanding of the present invention, reference is made to the following description of exemplary embodiments thereof, considered in conjunction with the accompanying drawings, in which.

DETAILED DESCRIPTION OF THE DRAWINGS

Although the present invention system and method can be embodied in many ways, the embodiments illustrated show only two exemplary embodiments. These embodiments are selected in order to set forth some of the best modes contemplated for the invention. The illustrated embodiments, however, are merely exemplary and should not be considered a limitation when interpreting the scope of the appended claims.

Figure 1:
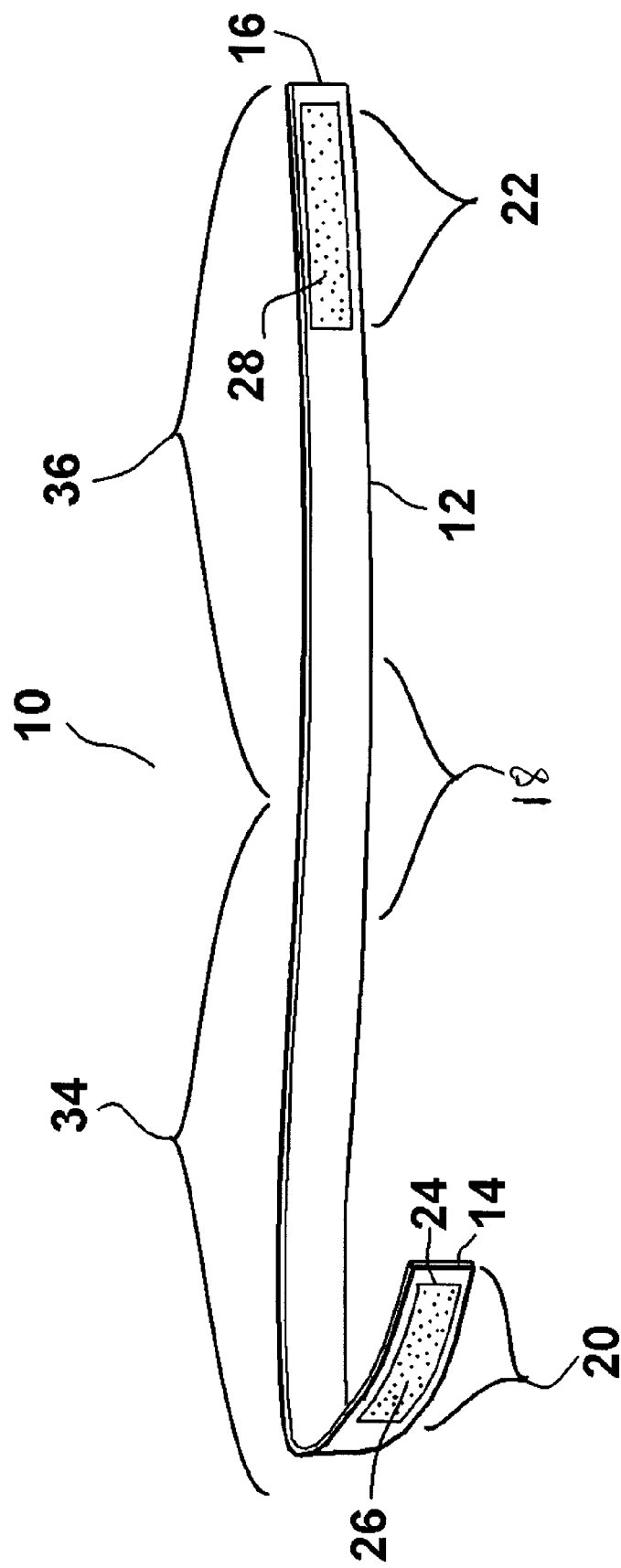
FIG. 1 is a perspective view of a first exemplary embodiment of a head restraint system.
Figure 2:
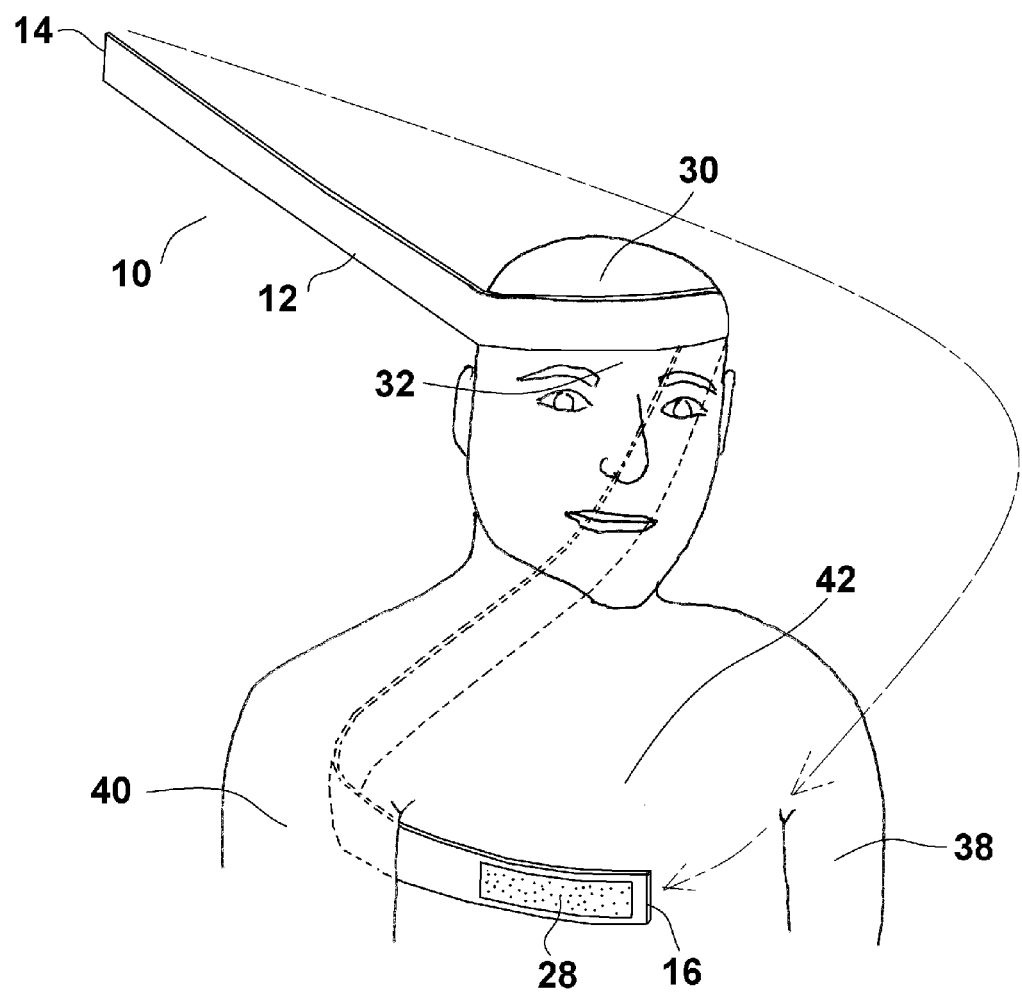
FIG. 2 is a perspective view of the first exemplary embodiment of a head restraint system being applied to the body of a user.
Figure 3:
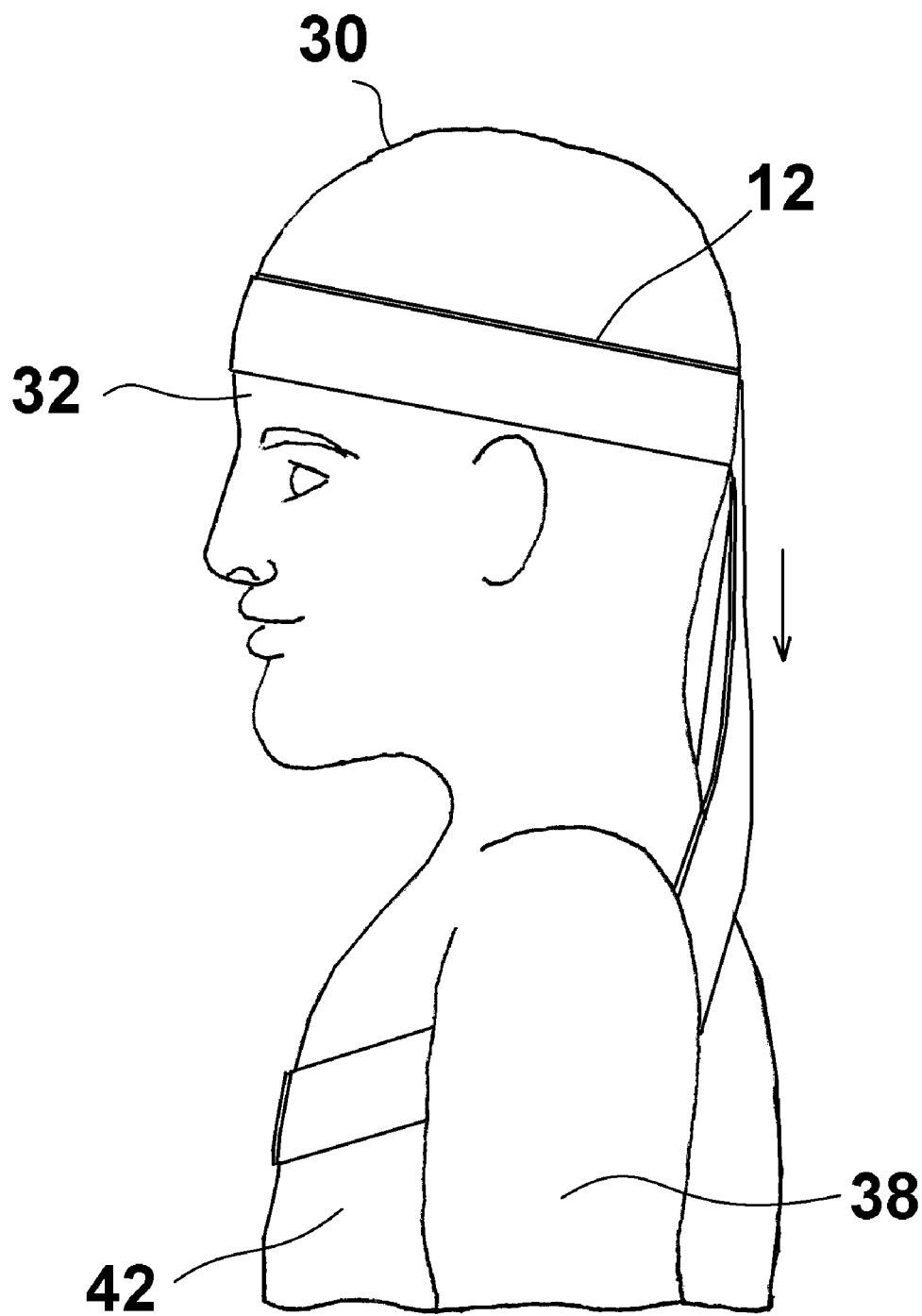
FIG. 3 is a side view of the first exemplary embodiment of a head restraint system fully applied to the body of a user.

Referring to FIG. 1 in conjunction with both FIG. 2 and FIG. 3, a first embodiment of the present invention head restraint system 10 is illustrated. The head restraint system 10 includes the use of a strap 12. The strap 12 has a first end 14, a second end 16 and a length between the first end 14 and the second end 16. The length selected for the strap 12 depends upon the size of the person using the head restraint system 12. However, for most adult users, the strap 12 has an unstretched length of between four feet and six feet.

The strap 12 is a length of elastic webbing having a width of between one to three inches and an elastic stretch capacity of between 20% and 60%. Accordingly, the stated unstretched length of the strap 12 can be increased by applying tension to the strap 12 and stretching the strap 12 longer.

The strap 12 has a center section 18 disposed halfway between the first end 14 and the second end 16. The strap 12 also has a first attachment section 20 proximate the first end 14 and a second attachment section 22 proximate the second end 16. A fastener 24 is attached to the strap 12 near one or both of the attachment sections 20, 22. In the illustrated embodiment, the fastener 24 includes two segments of hook and loop fastening material 26, 28 that are sewn to the strap 12. A first segment of hook and loop fastening material 26 is sewn to the front of the strap 12 in the first attachment section 20. A second segment of hook and loop material 28 is sewn to the back of the strap 12 in the second attachment section 22. The use of hook and loop fastener material is merely exemplary. It should be understood that other fasteners, such as belt buckles, snaps, and connector clips can be used in place of the hook and loop material. What is of importance is that a fastener is provided that gives the first attachment section 20 of the strap 12 and the second attachment section 22 of the strap 12 the ability to interconnect in a variety of positions.

In order to utilize the head restraint system 10, the center section 18 of the strap 12 is placed against the forehead 32 of a person who is in need of support for his/her head 30. This roughly divides the strap 12 into two halves 34, 36. As such, the first half 34 of the strap 12 that terminates with the first end 14 is positioned on the right side of the head 30. Conversely, the second half 36 of the strap 12 that terminates with the second end 16 is positioned on the left side of the head 30. Both halves 34, 36 of the strap 12 are extended to the back of the head 30. Once behind the head 30, the first half 34 of the strap 12 and the second half 36 of the strap 12 are crossed.

The first end 14 of the strap 12 is then directed under the left arm 38 of the user so that the first end 14 of the strap 12 and the first attachment section 20 of the strap 12 are now in front of the user. The second end 16 of the strap 12 is directed under the right arm 40 of the user so that the second end 16 of the strap 12 and the second attachment section 22 of the strap 12 are also in front of the user. Once the first attachment section 20 and the second attachment section 22 are in front of the user, the user applies tension to the first half 34 and the second half 36 of the strap 12 by pulling on the strap 12. The amount of tension is increased until the tension lifts the user's head 30 into a desired forward facing orientation. Once the user's head 30 is in the desired orientation, the first attachment section 20 of the strap 12 and the second attachment section 22 of the strap 12 are joined together across the torso 42 of the user. Once so positioned, it will be understood that the strap 12 is now configured as a continuous loop. The loop begins at the first end 14 of the strap 12 where it rests upon the front of the user's torso 42. The loop continues as the strap 12 advances under the user's left arm 38, up to the right side of the head 30, across the forehead 32 to the left side of the head 30. The loop returns to the front of the user's torso 42 by crossing the back of the torso 42, and passing under the right arm 40. At this position, the first attachment section 20 and the second attachment section 22 are joined by the fastener 24 across the front of the torso 42.

Since the strap 12 passes under the user's arms 38, 40 and across the user's torso 42, the strap 12 is anchored to the user's torso 42. Likewise, the strap 12 passing over the user's forehead 32 anchors the strap 12 to the forehead 32. The user's head 30 and torso 42 are therefore mechanically interconnected by the strap 12. The strap 12 can be set either above or below most any shirt. The strap 12 holds the user's head in an upright orientation. However, the strap 12 has elastic characteristics. As such, the user is free to move his/her head down against the bias of the strap 12. As soon as the effort is stopped, the bias of the strap 12 returns the user's head 30 to an upright position. The strap 12 therefore provides the user with the ability to move his/her head 30 down and from side to side as the strap 12 provides resistance to such movements. Since the strap 12 provides resistance to certain movements, but does not prevent those movements, the strap 12 can be used to exercise neck muscles and strengthen or rehabilitate those muscles.

Either by incidental use or by direction from a physical therapist, a user will can mover his/her head 30 against the elastic bias of the strap 12 to exercise the muscle groups that move the head 30 forward. The user can then try to slowly return the head to its upright position while resisting the elastic bias of the strap 12 in order to exercise the muscle groups that hold the head upright. For many users, this exercise will strengthen the muscle groups of the neck and will hopefully eliminate the future need for any head support.

In the embodiment of FIGS. 1, 2, and 3, the strap 12 directly contacts the head 30 of the user. A user may not want the strap 12 to directly contact his/her skin. One reason might be that the strap 12 may absorb sweat and may need laundering. Repeated laundering may adversely affect the elastic characteristics of the strap 12. As such, the present invention may also be configured with a hat to prevent direct contact between the user's head and the strap. Such an alternate embodiment is shown in FIG. 4.

Figure 4:
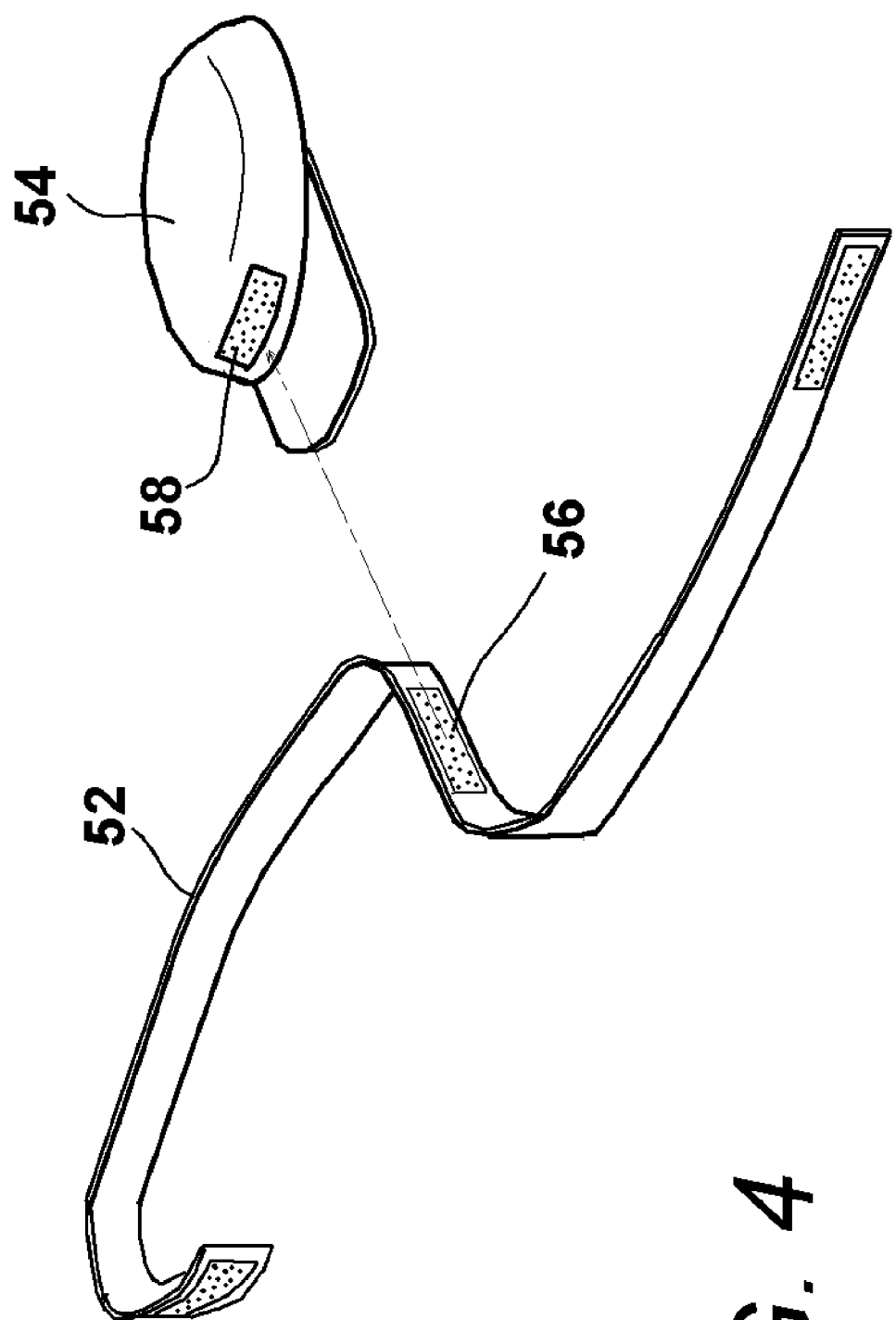
FIG. 4 is a perspective view of a second exemplary embodiment of a head restraint system.

Referring to FIG. 4, a head restraint system 50 is shown containing both a hat 54 and a strap 52. The strap 52 has the same construction as has been previously described in the earlier embodiment. However, the strap 52 now has a section of hook and loop fastening material 56 sewn to the strap 52 near its center.

The hat 54 has the construction of a traditional baseball cap. What is different is that the hat 54 also has a section of hook and loop fastening material 58 sewn to the front of the hat 54. The hook and loop fastening material 56 on the strap 52 engages the hook and loop fastening material 58 on the hat 54 and interconnects the strap 52 to the hat 54. The strap 52 is anchored to the user's torso in the manner previously explained for the earlier embodiment. The use of the hat 54 anchors the strap 52 to the user's head while prevents the strap 52 from directly touching the head of the user. The hat 54 also has the ability to cushion the contact between the user's head and the strap 52 to lessen the likelihood of contact sores.

It will be understood that the embodiments of the present invention that are illustrated and described are merely exemplary and that a person skilled in the art can make many variations to those embodiments. For instance, the length and width of the strap can be varied. Likewise, the fasteners used to secure the strap into a loop can be varied. All such embodiments are intended to be included within the scope of the present invention as defined by the claims.

What is claimed is:

1. For a user having a torso, arms, and a head with a forehead, a method of supporting the user's head in an upright position, the method comprising:
    providing a single continuous strap having a first end, a second end, a first attachment section proximate said first end, a second attachment section proximate said second end and a center section between said first attachment section and said second attachment section;
    placing the center section of said strap on a front of the forehead of the user;
    extending said strap behind the user and crossing said strap behind the user;
    extending the first end and the second end of said crossed strap under the respective arms to a position in front of the torso;
    applying tension to the first end and the second end of said strap therein moving the head of the user into an upright orientation; and
    connecting the first end and the second end by joining said first attachment section to said second attachment section across the torso to anchor said strap to the torso of the user to maintain the tension in said strap.

2. The method according to claim 1, wherein said joining said first attachment section to said second attachment section includes providing a fastener that mechanically interconnects said first attachment section to said second attachment section.

3. The method according to claim 2, wherein said fastener is hook and loop material.

4. The method according to claim 1, wherein placing the center section of said strap on the front of the forehead of the user includes placing said strap in direct contact with the forehead.

5. The method according to claim 1, further comprising providing a hat and placing said hat on the head of the user, wherein said placing the center section of said strap on the forehead of the user includes placing the center section of said strap in contact with a portion of said hat that is in contact with the forehead of the user.

6. The method according to claim 5, further comprising mechanically interconnecting said strap to said hat.

7. The method according to claim 1, wherein said strap has elastic characteristics that enable said strap to increase in length by at least 40 percent when stretched.

8. For a user having a torso, arms, and a head with a forehead, a method of supporting the user's head in an upright position, the method comprising:
    providing a single continuous strap having a first half that terminates with a first end, a second half that terminates with a second end, wherein said strap has elastic characteristics that enable said strap to elastically stretch under tension;
    placing a center section of said strap on a front of the forehead of the user;
    extending said strap behind the user;
    crossing said first half of said strap and said second half of said strap behind the user;
    extending said first half and said second half of said crossed strap under the respective arms to a position in front of the torso;
    applying tension to said first half and said second half of said strap to move the head of the user into an upright orientation; and
    joining said first half of said strap and said second half of said strap together across the torso by connecting the first end and the second end to anchor said strap to the torso of the user to maintain said tension in said strap.

9. The method according to claim 8, wherein said joining said first half of said strap and said second half of said strap together includes providing a fastener that mechanically interconnects said first half of said strap and said second half of said strap together.

10. The method according to claim 8, further comprising providing a hat and placing said hat on the head of the user, wherein said placing the center section of said strap on the front of the forehead of the user includes placing the center section of said strap in contact with a portion of said hat that is in contact with the front of the forehead of the user.

11. The method according to claim 10, wherein said placing the center section of said strap in contact with the portion of said hat includes interconnecting said strap with the portion of said hat.

12. For a user having a torso, arms, and a head with a forehead, a method of supporting the user's head in an upright position, the method comprising:
    providing a single continuous elastic strap having a first half that terminates with a first end, a second half that terminates with a second end;
    placing a center section of said elastic strap on a front of the forehead of the user;
    extending said elastic strap behind the user;
    crossing said first half of said elastic strap and said second half of said elastic strap behind the user;
    extending said first half and said second half of said crossed elastic strap under the respective arms to a position in front of the torso; and
    joining said first half of said elastic strap and said second half of said elastic strap together across the torso by connecting the first end and the second end to anchor said elastic strap to the torso of the user, wherein said elastic strap provides resistance to any drooping of the head.

13. The method according to claim 12, wherein said joining said first half of said elastic strap and said second half of said elastic strap together includes providing a fastener that mechanically interconnects said first half of said elastic strap and said second half of said elastic strap together.

* * * * *